(12) United States Patent
Bastian et al.

(10) Patent No.: US 8,008,475 B1
(45) Date of Patent: Aug. 30, 2011

(54) METHOD FOR ISOLATING AND PURIFYING NUCLEIC ACIDS ON SURFACES

(75) Inventors: Helge Bastian, Mettmann (DE); Simone Gauch, Pasadena, CA (US); Uwe Oelmüller, Erkrath (DE); Susanne Ullmann, Erkrath (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 09/536,736

(22) Filed: Mar. 28, 2000

Related U.S. Application Data

(63) Continuation of application No. PCT/EP98/06756, filed on Oct. 23, 1998.

(30) Foreign Application Priority Data

Oct. 23, 1997 (DE) .................................. 197 46 874

(51) Int. Cl.
   *C07H 21/00* (2006.01)
(52) U.S. Cl. .................. 536/25.4; 210/650; 210/679
(58) Field of Classification Search ............... 435/6, 6.1, 435/91, 259; 436/94; 536/23.1
   See application file for complete search history.

(56) References Cited

U.S. PATENT DOCUMENTS

| | | | | |
|---|---|---|---|---|
| 5,004,543 A | * | 4/1991 | Pluskal et al. | 210/490 |
| 5,187,083 A | * | 2/1993 | Mullis | 435/91.1 |
| 5,234,809 A | * | 8/1993 | Boom et al. | 435/91.2 |
| 5,234,824 A | * | 8/1993 | Mullis | 435/91.1 |
| 5,658,548 A | * | 8/1997 | Padhye et al. | 423/335 |
| 5,728,531 A | * | 3/1998 | Yamada et al. | 435/6 |
| 5,858,700 A | * | 1/1999 | Ausich et al. | 435/67 |
| 5,869,073 A | * | 2/1999 | Sawan et al. | 424/406 |
| 5,985,572 A | * | 11/1999 | MacFarlane | 435/6 |
| 6,028,186 A | * | 2/2000 | Tasset et al. | 536/24.31 |
| 6,258,531 B1 | * | 7/2001 | Bienhaus et al. | 435/6 |
| 6,383,393 B1 | * | 5/2002 | Colpan et al. | 210/656 |

FOREIGN PATENT DOCUMENTS

| | | | | |
|---|---|---|---|---|
| DE | 19746874.8 | | 4/1999 | |
| EP | 0431905 A1 | * | 6/1991 | |
| EP | 0442026 A2 | * | 8/1991 | |
| EP | 587951 | * | 3/1994 | .................. 435/455 |
| WO | WO 87/06621 | | 11/1987 | |
| WO | WO 95/21849 | | 8/1995 | |
| WO | WO 96/41810 | * | 12/1996 | .................. 536/23.1 |
| WO | WO 97/08547 | * | 3/1997 | .................. 436/174 |

OTHER PUBLICATIONS

Jakobi et al. Filter-supported preparation of Lmbda phage DNA. Anal. Biochem. vol. 175:196-201, 1988.*
Holmes et al. Accumulation of DNA damages in aging paramecium tetraurelia. Mol. Gen. Genet. vol. 204:108-114, Jul. 1986.*
Millipore Catalog, 1995, available at URL: millipore.com/catalogue.nsf/docs/pf185 and C7485.*
Pfister et al. (J. Biol. Chem. 1996; 271:1687-94.*
RNeasy Mini Handbook, Qiagen, 1999: 1-12.*
Birnboim, *Methods in Enzymology*, 100: 243-255 (1983).
Bresters et al., *J. Med. Virol.*, 43: 262-268 (1994).
Collins et al., *Nucl. Acids Res.*, 25(15): 2979-2984 (1997).
Colpan and Riesner, *J. Chromatog.*, 296: 339-353 (1984).
Holland et al., *Proc. Natl. Acad. Sci. USA*, 88: 7276-7280 (1991).
Kievits et al., *J. Virol. Methods.*,35: 273-286 (1991).
Livak et al., *PCR Methods Applic.*, 4: 357-362 (1995).
Marko et al., *Analyt. Biochem.*, 121: 382-387 (1982).
Moreau et al., *Analyt. Biochem.*, 166: 188-193 (1987).
Uyttendaele et al., *J. Appl. Bacteriol.*, 77: 694-701 (1994).
Vogelstein et al., *Proc. Natl. Acad. Sci. USA*, 76: 615-619 (1979).

* cited by examiner

*Primary Examiner* — Jim Ketter
(74) *Attorney, Agent, or Firm* — Fanelli Haag PLLC

(57) ABSTRACT

The present invention involves a process for the isolation of nucleic acids on surfaces by means of at least the following steps: charging of a surface from a given direction with nucleic acids; immobilization of the nucleic acids on the surface; release of the immobilized nucleic acids from the surface; and removal of the released nucleic acids essentially in the direction of charging. Preferably the loading takes place from the top.

70 Claims, 7 Drawing Sheets

# METHOD FOR ISOLATING AND PURIFYING NUCLEIC ACIDS ON SURFACES

CROSS-REFERENCE TO RELATED APPLICATIONS

This application is a continuation of pending International application no. PCT/EP98/06756, filed Oct. 23, 1998 and designating the United States and claiming priority to German application DE 19746874.8-44, filed Oct. 23, 1997.

FIELD OF THE INVENTION

The present invention relates to a new process for the isolation and purification of nucleic acids on surfaces.

BACKGROUND OF THE INVENTION

The isolation and purification of nucleic acids from biological and clinical sample material is of crucial importance for fields of work in which operating techniques based on nucleic acids are employed, or in which technologies based on nucleic acids are actually the key to access. Examples include paternity analysis, tissue typing, identification of hereditary diseases, genome analysis, molecular diagnostics, determination of infectious diseases, animal and plant breeding, transgenic research, basic research in biology and medicine, as well as numerous related areas. In general, a difficulty is encountered in preparing biological or clinical sample materials in such a manner that the nucleic acids contained in them can be used directly in a desired analytical procedure.

The state of the art already includes many processes for the purification of DNA. For example, we know how to purify plasmid DNA for the purpose of cloning—and other experimental processes as well—according to the method of Birnboim (*Methods in Enzymology*, 100: 243 (1983)). In this process, a cleared lysate of bacterial origin is exposed to a cesium chloride gradient and centrifuged for a period of 4 to 24 hours. This step is usually followed by the extraction and precipitation of the DNA. This process is associated with the disadvantages that it is very apparatus-intensive, and it takes a great deal of time, is expensive to run and cannot be automated.

Other methods in which cleared lysates are used to isolate DNA are based on ion-exchange chromatography (e.g., Colpan et al., *J. Chromatog.*, 296:339 (1984)) and gel filtration (e.g., Moreau et al., *Analyt. Biochem.*, 166:188 (1987)). These processes are primarily alternatives to the cesium chloride gradients; however they require an extensive solvent supply system, and a precipitation of the DNA fractions is necessary, since these usually contain salts in high concentrations and are extremely diluted solutions.

Marko et al. *Analyt. Biochem.*, 121:382 (1982), and Vogelstein et al., *Proc. Nat. Acad. Sci.*, 76:615 (1979), have found that if the DNA from extracts containing nuclei acids is exposed to high concentrations of sodium iodide or sodium perchlorate, the DNA alone will adhere to small glass scintillation tubes, fiberglass membranes or fiberglass sheets that have been finely particulated by mechanical means, while RNA and proteins do not. The DNA that has been bound in this manner can be eluted, for example, with water.

For example, in international publication WO 87/06621, the immobilization of nucleic acids on a PVDF membrane is described. However, the nucleic acids bound to the PVDF membrane are not eluted in the next step; instead the membrane, together with all the bound nucleic acids is introduced directly into a PCR reaction. Finally, in this international patent application and in the other literature, it is stated that hydrophobic surfaces or membranes must in general be wetted beforehand with water or alcohol, in order to be able to immobilize the nucleic acids with yields that are satisfactory.

On the other hand, for a number of modern applications, such as, for example, the PCR, reversed transcription PCR, SunRise, LCR, branched-DNA, NASBA, or TaqMan technologies and similar real-time quantification methods for PCR, SDA, DNA and RNA chips and arrays for gene expression and mutation analyses, differential display analyses, RFLP, AFLP, cDNA synthesis or substractive hybridization, it is absolutely necessary to be able to release the nucleic acids directly from the solid phase. In this connection, WO 87/06621 teaches that, while the nucleic acids can indeed be recovered from the membranes used in the process, this recovery is fraught with problems and is far from suited to the quantitative isolation of nucleic acids. In addition, the nucleic acid obtained in this manner is, comparatively, extremely diluted, which makes subsequent isolation and concentration steps absolutely necessary.

For the reasons stated above, the processes known from the state of the art do not constitute—particularly with regard to automation of the process for obtaining nucleic acids—a suitable starting point for an isolation of nucleic acid that is as simple and productive as possible from the point of view of process engineering.

SUMMARY OF THE INVENTION

The purpose of this invention is therefore to overcome the disadvantages of the processes known from the state of the art for the isolation of nucleic acids and to make available a process which is capable of being almost completely automated without substantial additional technical expenditure.

According to the present invention, the aforementioned disadvantages are solved by the processes, isolation and/or reaction devices used, automatic apparatus, and kits according to the description, drawings and claims below.

In this connection, the invention involves a process which uses surfaces, e.g., porous membranes, on which the nucleic acids can be immobilized in a simple way from a sample containing the nucleic acids and can again be released by means of simple procedural steps. In particular, the simple procedure on which the invention depends makes it possible to carry out the process completely automatically.

Another aspect of this invention is, in particular, to bind nucleic acids to an immobile phase—especially to a membrane—in such a manner that in a subsequent reaction step they can be released immediately from this phase and, if desired, used in other applications, such as, for example, restrictive digestion, RT, PCR or RT-PCR, or any other suitable analytic or enzymatic reaction named above.

The present invention provides a procedure for isolating nucleic acids by means of the following steps:
  loading a surface from a given direction with nucleic acids;
  immobilizing the nucleic acids on the surface;
  releasing the immobilized nucleic acids from the surface; and
  removing the released nucleic acids from the surface essentially in the direction of the loading.

Preferably the charging (loading) takes place from the top. In this case, gravity can be used to collect the buffer to be used for the release and for the release itself. Between the immobilizing and the release steps, washing of the immobilized nucleic acids can take place with at least one washing buffer.

For each washing buffer the washing includes preferably the following steps:
  applying a predetermined volume of washing buffer to the surface, and
  pulling the washing buffer through the surface with suction.

Loading and immobilizing the nucleic acids may again include the following steps:
  mixing the nucleic acids with an immobilization buffer,
  applying the nucleic acids with the immobilization buffer to the surface, and
  drawing the liquid components through the surface essentially in the direction of the loading.

The procedure has the great advantage that it can be easily automated, with the result that at least one of the steps can be carried out completely automatically by means of an automated apparatus. It is also possible that all the steps in the procedure can be carried out in a guided series of steps by an automated apparatus.

In these cases in particular, but also with manual operation, it is possible that a majority of the nucleic acids can be subjected to isolation at the same time.

Finally, in the process involved in this invention the following steps can be carried out at least once between the release and the removal steps:
  carrying out at least one chemical reaction with the nucleic acids;
  immobilization of the nucleic acids at the surface; and
  release of the immobilized nucleic acids from the surface.

As outlined above, the nucleic acid is essentially eluted (released) from the surface in the same direction from which it was applied and immobilized. By "the same direction" is meant basically any direction from an angle equal to or less than 180 degrees, so that during elution the nucleic acids do not penetrate the surface under any circumstances, but are removed from the surface in the opposite direction of the direction of charging in which they were applied to the surface. In preferred embodiments, on the other hand, the other buffers, i.e., the buffer in which the nucleic acids are to be found while charging, including in some cases a washing buffer, are drawn through the surface or otherwise transferred. When the isolation takes place on a membrane which is in a device, where the membrane covers the entire diameter (cross-section) of the device, then the preferred direction of charging is from the top. In this case, the removal step takes place again from the top. FIG. 2, for example, shows a funnel-shaped isolation device which is charged from the top and with which the removal of the nucleic acids takes place in an upward direction.

It is to be understood, however, that other arrangements are conceivable, i.e., removal of the nucleic acids from below. It is, for example, conceivable that a buffer containing nucleic acids, such as a lysate buffer, can be drawn from a reaction device directly upwards into an isolation device by means of a vacuum apparatus, so that the nucleic acids are bound to the underside of a membrane in the isolation device. In such a case, the removal of the nucleic acids from the surface takes place by means of an elution buffer drawn from below, which after release of the nucleic acids is then drained downward into a device. In this case, the removal of the nucleic acids takes place in a downward direction.

Even a lateral removal of the nucleic acids is possible, for example, when a column lying on its side with a membrane positioned for a flow-through process is charged with a lysate and the horizontally placed column is subsequently rinsed by an elution buffer on the side of the membrane on which the nucleic acids are bound.

An example for the maximum angle of 180 degrees possible is an inclined surface with a surface suitable for the binding of nucleic acids over which the various solutions or buffers flow downwards. Like all buffers, the elution buffer, too, comes from one side and flows down the other side. In this case, the direction of the entering stream of the buffer and the exiting stream of the buffer containing the nucleic acids form an angle of 180 degrees; the removal, however, always takes place on the same side of the surface as the immobilization.

By nucleic acids, in the sense of the present invention, all aqueous or other solutions of nucleic acids, as well as all nucleic acids containing biological materials or biological samples are included. In the sense of the present invention, this term would apply to free nucleic acids, or to a sample containing a nucleic acid or to a substance obtained by means of sampling or a sampling procedure which contains nucleic acids, which can serve as suitable educts for in vitro transcriptions, PCR reactions, or cDNA syntheses.

By biological material or biological sample is meant, e.g., plasma, body fluids (such as blood, saliva, urine, feces, sperm), cells, serum, leukocyte fractions, crusta phlogistica, smears, tissue samples of every kind, plants and parts of plants, bacteria, viruses, yeasts, etc., as they are set forth, for example, in the European patent publication No. EP 743 950 A1, which is incorporated herein by reference.

By nucleic acids, in the sense of the present invention, are meant all possible kinds of nucleic acids, as, e.g., ribonucleic acids (RNA) and deoxyribonucleic acids (DNA) in all lengths and configurations as double-stranded, single-stranded, circular and linear, branched, etc., monomer nucleotides, oligomers, viral and bacterial DNA and RNA, as well as genomic or other non-genomic DNA and RNA from animal and plant cells or other eukaryotes, t-RNA, mRNA in processed and unprocessed form, hn-RNA, rRNA, and cDNA, as well as all other imaginable nucleic acids.

In the process according to this invention, the sample containing nucleic acids described above is introduced into a solution which contains the appropriate salts or alcohol(s), then, in appropriate cases, elutes and mixes the sample and passes the mixture achieved in this way by means of a vacuum, through the use of a centrifuge, by means of positive pressure, by capillary forces, or by other appropriate procedures through a porous surface, by which process the nucleic acids are immobilized on the surface.

Suitable salts for the immobilization of nucleic acids on membranes include salts of the alkaline or alkaline earth metals with mineral acids, in particular alkaline or alkaline earth halogenides or sulfates, with the halogenides of sodium or potassium or magnesium sulfate being especially preferred.

Also suitable for carrying out the process according to the invention are salts of monobasic or polybasic acids or polyfunctional organic acids with alkaline or alkaline earth metals. These include, in particular, salts of sodium, potassium or magnesium with organic dicarboxylic acids (e.g., oxalic acid, malonic acid or succinic acid) or with hydroxycarboxylic or polyhydroxy-carboxylic acids (e.g., preferably, with citric acid).

The use of so-called chaotropic agents has proved to be especially effective. Chaotropic substances are capable of disturbing the three-dimensional structure of hydrogen bonds. This process also weakens the intramolecular binding forces that participate in forming the spatial structures— including primary, secondary, tertiary or quaternary structures—in biological molecules. Chaotropic agents of this kind are known to those skilled in the art (see, e.g., Rompp,

*Lexikon of Biotechnologie*, published by H. Dellweg, R. D. Schmid and W. E. Fromm, Thieme Verlag, Stuttgart 1992).

The preferred chaotropic substances for use with this invention are, for example, salts from the trichloroacetate, thiocyanate, perchlorate or iodide group or guanidinium hydrochloride and urea. The chaotropic substances are used in a 0.01-molar to 10-molar aqueous solution, preferably in a 0.1 M to 7 M aqueous solution and most preferably in a 0.2 M to 5 M aqueous solution. The chaotropic agents mentioned above can be used alone or in combinations. In particular, a 0.01 M to 10 M aqueous solution, preferably a 0.1 M to 7 M aqueous solution, and most preferably a 0.2 M to 5 M aqueous solution of sodium perchlorate, guanidinium hydrochloride, guanidinium isothiocyanate, sodium iodide, or potassium iodide may be used.

Suitable alcohols useful in carrying out the process according to the invention include, first of all, all the hydroxyl derivatives of aliphatic or acyclic saturated or unsaturated carbohydrates. It is initially unimportant whether the compound in question contains one, two, three or more hydroxyl groups—such as polyvalent C1-C5 alkanols, including ethylene glycol, propylene glycol or glycerine.

In addition, the alcohols according to the invention include the sugar derivates, the so-called aldites, as well as the phenols, such as polyphenol.

Among the hydroxyl compounds mentioned above, the C1-C5 alkanols, such as methanol, ethanol, n-propanol, tertiary butanol and the pentanols are especially preferred.

Immobilization can be carried out under acid, neutral, or alkaline conditions. Thus, the pH in immobilization can lie between pH 3 and pH 11; in preferred embodiments, immobilization takes place at a pH between 4 and 8. If RNA is to be isolated, the pH will preferably lie in the neutral range, while with the isolation of DNA, an acid pH can be more favorable. Thus, the pH for the isolation of RNA can, for example, lie in the area of pH 6 to 8, preferably from pH 6.5 to 7.5. For DNA isolations, the pH will lie most favorably in the range between pH 4 and pH 8, preferably between pH 4 and pH 6. For the purposes of the present invention, the term hydrophilic applies to such materials or membranes which by virtue of their chemical nature mix easily with water or absorb water.

For the purposes of the present invention, the term hydrophobic applies to such materials or membranes which by virtue of their chemical nature do not penetrate into water—or vice versa—and which are not able to remain dissolved in water.

By the word surface, in the sense of the present invention, is meant any microporous-separating layer. In the case of a membrane, the surface consists of a film of a polymer material. The polymer will be preferably composed of monomers with polar groups.

In another embodiment of the process according to the invention, the concept of surface in the broader sense includes a layer of particles or a granulate or even fibers such as, e.g., silica gel fleece.

In connection with the use of hydrophobic membranes, in the sense of the present invention, those membranes are preferred which consist of a hydrophilic substance and which can be rendered hydrophobic by a subsequent chemical treatment which is well known from the current state of the art, such as hydrophobisized nylon membranes which are commercially available. For the purposes of this invention, hydrophobisized membranes include, in general, those membranes which may or may not have been hydrophilic to begin with and are coated with the hydrophobic coating agents mentioned below. Hydrophobic coating agents of this kind cover hydrophilic substances with a thin layer of hydrophobic groups, such as fairly long alkyl chains or siloxane groups. Many suitable hydrophobic coating agents are known in the art; for purposes of the invention, these include paraffins; waxes; metallic soaps etc., if necessary with additives of aluminum or zirconium salts; quaternary organic compounds; urea derivates; lipid-modified melamine resins; silicones; zinc-organic compounds; glutaric dialdehyde; and similar compounds.

In addition, the hydrophobic membranes that can be used for purposes of the invention are those that have been made hydrophobic and whose basic material contains polar groups. According to these criteria, for example, materials from the following group—particularly hydrophobisized ones—are suitable for use with the invention: Nylon, polysulfones, polyether sulfones, polycarbonates, polyacrylates and acrylic acid copolymers, polyurethanes, polyamides, polyvinyl chloride, fluorocarbonates, polytetrafluoroethylene, polyvinylidene fluoride, polyvinylidene diflouride, ethylene tetrafluoroethylene, polyethylene chlorotrifluoroethylene copolymerisate or polyphenylene sulfide, and cellulose-mix esters or nitrocelluloses as well as hydrophobisized glass fiber membranes, with hydrophobisized nylon membranes being especially preferred.

Preferred hydrophilic surfaces include in and of themselves hydrophilic materials and also hydrophobic materials that have been made hydrophilic. For instance, the following substances can be used: hydrophilic nylon, hydrophilic polyether-sulfones, hydrophilic polycarbonates, polyesters, hydrophilic polytetrafluoro-ethylenes on polypropylene tissues, hydrophilic polytetrafluorethylenes on polypropylene fleece, hydrophilisized polyvinylidene fluoride, polyvinylidene difluoride, hydrophilisized polytetrafluorethylenes, hydrophilic polyamides.

The membranes that are used in the process according to the invention have, for example, a pore diameter of 0.001 to 50 μm, preferably 0.01 to 20 μm and most preferably 0.05 to 10 μm.

For washing buffers, the salts or alcohols, phenols or polyphenols described above can be used. The temperatures in the washing step will usually be within the range from 10° to 30° C.; higher temperatures can also be used successfully.

Suitable eluting agents for the elution of bound nucleic acids for the purposes of the invention are water or aqueous salt solutions. As salt solutions, buffer solutions that are known in the art are used, such as morpholinopropane sulfonic acid (MOPS), tris(hydroxymethyl)aminomethane (TRIS), 2-[4-(2-hydroxyethyl)piperazino]ethane sulfonic acid (HEPES) in a concentration from 0.001 to 0.5 Mol/liter, preferably 0.01 to 0.2 Mol/liter, most preferably 0.01-molar to 0.05-molar solutions. Also preferred for use are aqueous solutions of alkaline or alkaline earth metal salts—in particular, their halogenides, including 0.001 M to 0.5 M, preferably 0.01 M to 0.2 M, most preferably 0.01 M to 0.05 M—aqueous solutions of sodium chloride, lithium chloride, potassium chloride or magnesium dichloride. Also preferred for use are solutions of salts of the alkaline or alkaline earth metals with carboxylic or dicarboxylic acids, such as oxalic acid or acetic acid, solutions of sodium acetate or oxalate in water—in the range of concentrations mentioned above—for example, 0.001 to 0.5 M (preferably 0.01- to 0.2-molar, and most preferably 0.01- to 0.05-molar).

Pure water is especially preferred as a means of elution, e.g., demineralized, double distilled, or Millepore filtered water.

Elution can be carried out successfully at temperatures of from 10° to 70° C., for example, between 10° and 30° C., and even at higher temperatures. Elution with steam is also possible.

With regard to the individual steps, the process according to the invention can be performed as follows:

The lysate of the sample used for the recovery of the nucleic acids or the originally free nucleic acid(s) is/are pipetted, for example, in a (plastic) column, in which the membrane is fastened—for example, on the floor. It is more efficient if the membrane is fastened to a grid, which serves as a mechanical support. The lysate is then conducted through the membrane, which can be achieved by applying a vacuum at the outlet of the column. The transport can also be accomplished by applying positive pressure to the lysate. In addition—as mentioned above—the transport of the lysate can take place by centrifuging or by the effect of capillary forces. The latter can be produced, for example, with a sponge-like material which is introduced below the membrane, in contact with the lysate or filtrate.

The added washing step in the preferred embodiments of the invention can take place by having the washing buffer transferred through the surface or membrane, or by having it remain on the same side of the surface as the nucleic acids. Where the washing buffer is passed or drawn through the membrane, this can take place in a variety of ways, e.g., by a sponge mounted on the other side of the membrane, by a vacuum or high-pressure apparatus, or by a centrifuge or gravity.

The advantage of this arrangement is that it is simple, reliable and provides handy means for removing the filtrate—in one embodiment, simply by removing a sponge, which is now more or less saturated with the filtrate, and which can be easily be exchanged. It should be clear at this point that the column can be operated continuously or batch-wise and that both these modes of operation can be fully automated, until the membrane is completely saturated with nucleic acid.

The last step is the elution of the nucleic acid, which can be drawn off or removed by a pipette or removed upward in some other way. In any case, what is essential for the elution step, in the procedure on which this invention is based, is that the nucleic acids are removed from the same side of the membrane from which they were applied to the membrane, i.e., that there is no passage of nucleic acids through the membrane. This series of procedures makes it possible to transfer all the fluids no longer needed, such as the original lysis buffer and the washing buffers, by vacuum or gravity to the "waste side" of the membrane, while the eluate remains on the other side. An apparatus of this kind makes it possible to automate the process of this invention in a particularly simple way, since a pipetting apparatus for the addition of the lysate and the removal of the eluate has to be provided only on one side of the surfaces; the other side of the surface, on the other hand, does not have to have any "clean area". In this way, by spatial separation, a contamination-free isolation of nucleic acids, especially freedom from RNase, can be assured by very simple means. Moreover, the isolation devices, e.g., cleansing columns, do not have to be repositioned, on the one hand to get rid of waste, on the other, to collect the eluate through the same opening of the device. This, too, means a simplification of the process of automating the procedure.

The capture of fractions that contain the desired nucleic acids in highly diluted solutions and require a subsequent concentration becomes completely unnecessary with the process according to the invention; instead, the desired nucleic acids are obtained in solutions containing little or no salt, in very small volumes, which is of great advantage for all molecular biological analytic procedures, since these procedures demand pure nucleic acids in the smallest possible volumes with a simultaneously high concentration. In order to achieve the goal of having the smallest amounts of eluate possible, those membranes are particularly preferred as surfaces which are as thin as possible, so that only a little fluid can collect in them. Less preferred, on the other hand, are fleeces such as silica gel fleeces, since these can absorb a relatively large amount of eluate, a condition which makes the removal of the eluate upwards more difficult, and which disadvantageouslincreases the necessary amount of eluate.

Moreover, the present invention has the advantage that, when the device is placed in a vertical position (the membrane then being in horizontal position), the space above the membrane can be used as a reaction area. Thus, for example, after the isolation and release of the nucleic acids obtained according to the basic process of the invention, it is possible not only to leave the nucleic acids in place but also to subject the nucleic acids, in the same apparatus or isolation device, to one or more molecular-biological applications, such as restrictive digestion, RT, PCR, RT-PCR, or enzymatic reactions. The nucleic acids thus treated may then be bound to the membrane again, in some cases washed as described previously and subsequently eluted, to isolate or analyze them, by means of, e.g., spectroscopy, fluorometry, or similar techniques of measurement.

The nucleic acids isolated pursuant to this invention are free from enzymes which decompose nucleic acids, and they have a level of purity which is so high that they can immediately be treated and processed in the most varied ways.

The nucleic acids produced according to this invention can be used for cloning, and can serve as substrates for the a variety of enzymes, such as DNA polymerases, DNA restriction enzymes, DNA-ligase, and reverse transcriptase.

The nucleic acid preparations produced by the process of this invention are especially well suited for amplification, particularly for the PCR (polymerase chain reaction), strand displacement amplification, the rolling circle procedure, the ligase chain reaction (LCR), and similar procedures.

In addition, the process of the invention is particularly well suited to the preparation of nucleic acids for use in diagnosis, particularly for a diagnostic procedure which is characterized by the fact that the nucleic acid purified by the process according to the invention must be amplified in a subsequent step, and the nucleic acid amplified in this way is then subsequently or immediately detected (z. B. Holland, P. M. et al., *Proc. Natl. Acad. Sci.,* 88:7276-7280 (1991); Livak, K. J. et al., *PCR Methods Applic.,* 4:357-362 (1995); Kievits, T. et al., *J. Virol. Meth.,* 35:273-286 (1991); Uyttendaele, M. et al., *J. Appl. Bacteriol.,* 77:694-701 (1994)).

Furthermore, the process of the present invention is particularly well suited for the preparation of nucleic acids which can be subjected in a subsequent step to a signal amplification step based on a hybridization reaction, which is especially characterized by the fact that the nucleic acids produced by the process of this invention can be brought into contact with "branched nucleic acids," especially branched DNA or branched RNA or dendritic nucleic acids, as described, for example in the following articles: Bresters, D. et al., *J. Med. Virol.,* 43 (3):262-286 (1994); Collins M. L. et al., *Nucl. Acids Res.,* 25(15):2979-2984 (1997), and that the signal which arises can be detected.

An example of automation of the process according to the invention is described below, and examples of how to perform the process with different surfaces and nucleic acid samples are also described. In this description reference is made to the attached figures which illustrate the following.

DETAILED DESCRIPTION OF THE PREFERRED EMBODIMENTS

Figure 1:
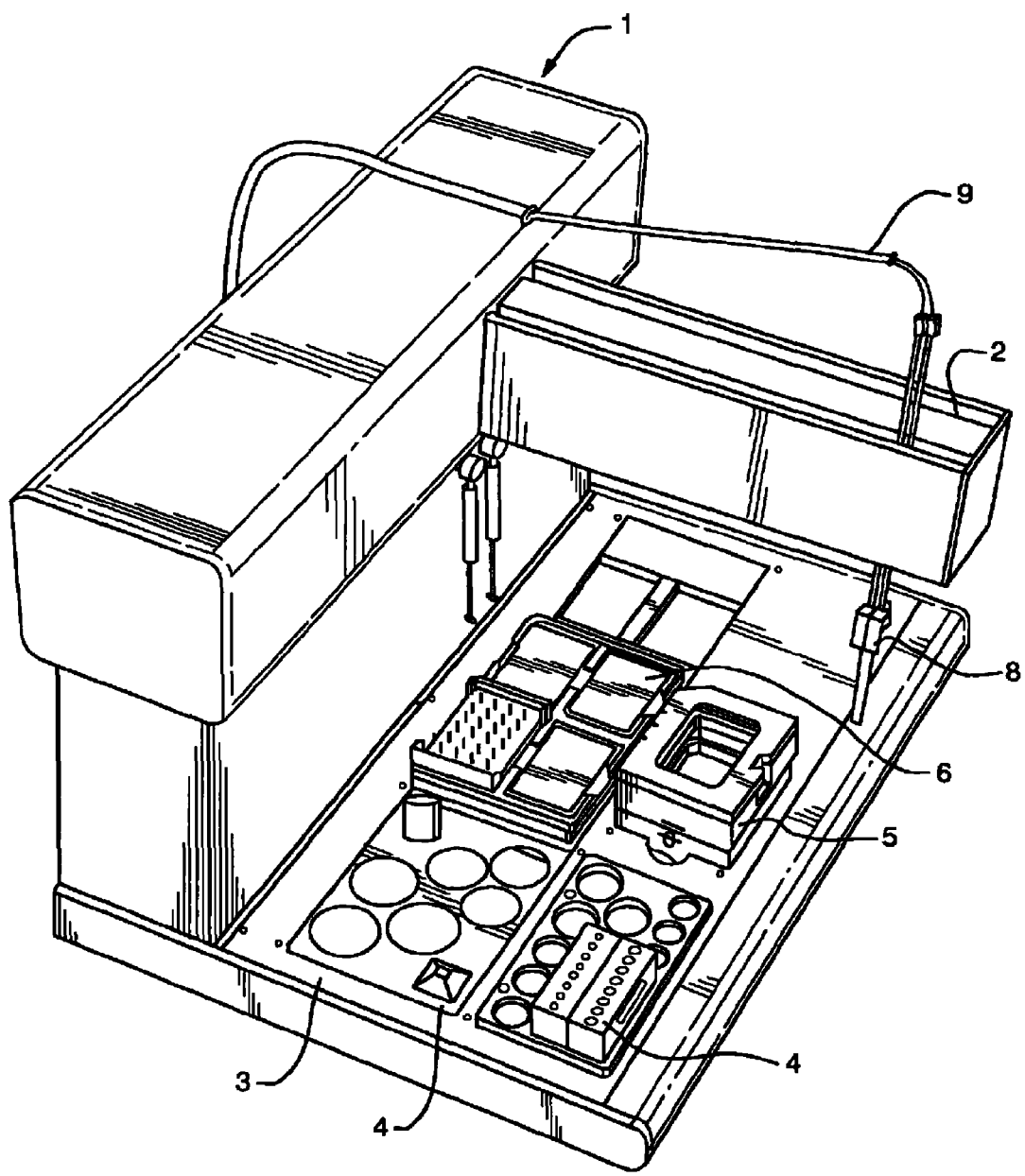
FIG. 1 illustrates an automatic apparatus suitable for performing the process according to the invention in a perspective view.

The process according to the invention is preferably performed in an manner that is at least partially automated and preferably completely automated, in other words, automated for all steps. An example for suitable automatic equipment is illustrated in FIG. 1, in which a main part 1 is equipped with control electronics and driving engines with a work platform 3 and a movable arm 2. Various elements are positioned on the work platform, such as area 4 to hold various devices. A vacuum manifold 5 serves to absorb liquids from isolation devices placed above them and open at the bottom, or otherwise with the devices connected to the vacuum manifold. A shaker 6 is also provided, which can be used, e.g., to subject the biological samples to lysis. The isolation device assemblies used are, e.g., injection-molded parts with integrated isolation devices, in which the surfaces according to the invention are included. Typically configurations of 8, 12, 24, 48, 96 or up to 1536 isolation devices can be used, as these are seen in the formats of multi-well-plates currently available. Even higher numbers of isolation device might be possible in one plate, if the corresponding standards are available. With the aid of Luer-adapters it is, however, also possible to make individual bottoms of the assembly available and to equip these with one or more isolation devices as needed. Isolation devices used individually without Luer-adapters are also included in the invention.

Under a vacuum and dispensing mechanism 8 the isolation device assemblies are placed in the automatic apparatus and via these, liquids can be taken in and drained off. In this assembly several single vacuum tubes can be used, so as to make the simultaneous processing of an isolation or reaction device possible. The vacuum and dispensing mechanism 8 therefore acts as a pipette. Vacuum and pressure are fed to the vacuum and dispensing mechanism 8 via tube 9.

To isolate the nucleic acids, reaction devices with cells may for example be placed in the shaker/holder 6, into which lysis buffers are introduced with the help of the dispensing mechanism. After mixing, the cell lysates are transferred to isolation devices. The lysis buffer is subsequently passed through the surfaces in the isolation devices. Subsequently, the surfaces may be washed with a washing buffer in order to remove cell lysate residue, in which also the washing buffer is drained off downward. Finally an elution buffer is dispensed into the isolation devices and after repeated shaking the separated nucleic acids are removed from the top and transferred to collection tubes.

Usually, disposable tips are used on the vacuum and dispensing mechanism 8 to prevent contamination of the samples.

Figure 2A:
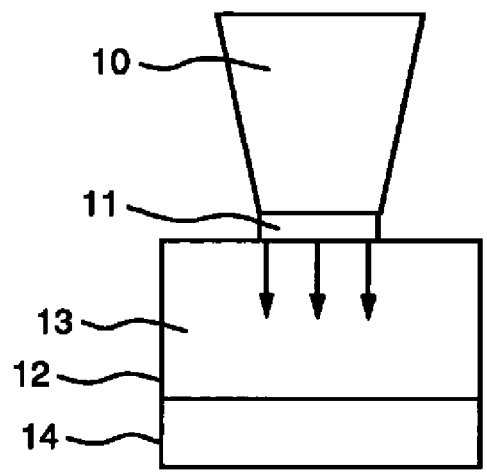
FIG. 2 shows a first embodiment of an isolation device and collection tube for performing the process according to the invention.
Figure 2B:
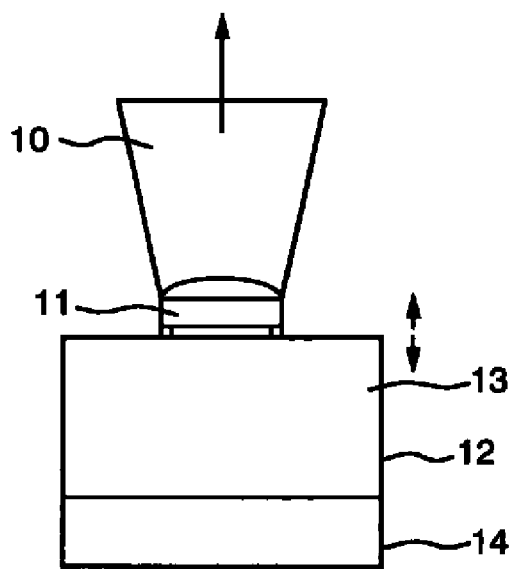
Figure 3A:
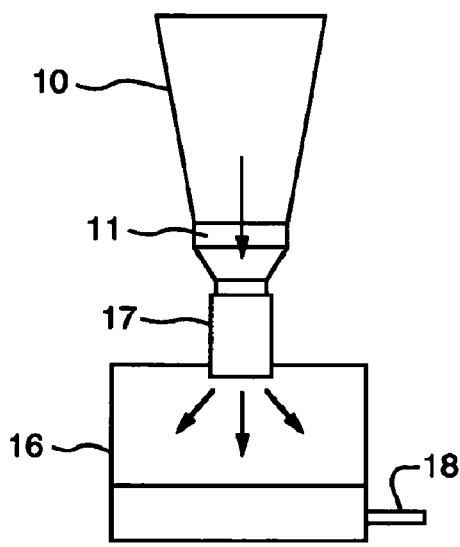
FIG. 3 shows a second embodiment of an isolation device and collection tube for performing the process according to the invention.
Figure 3B:
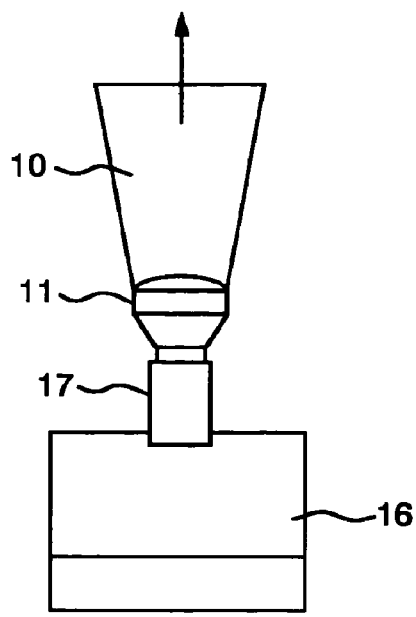
Figure 4A:
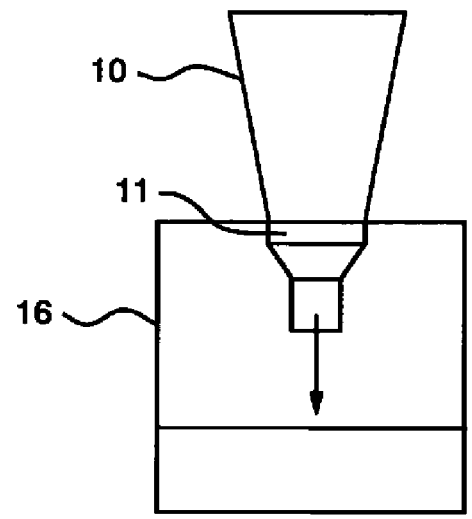
FIG. 4 shows a third embodiment of an isolation device and collection tube for performing the process according to the invention.
Figure 4B:
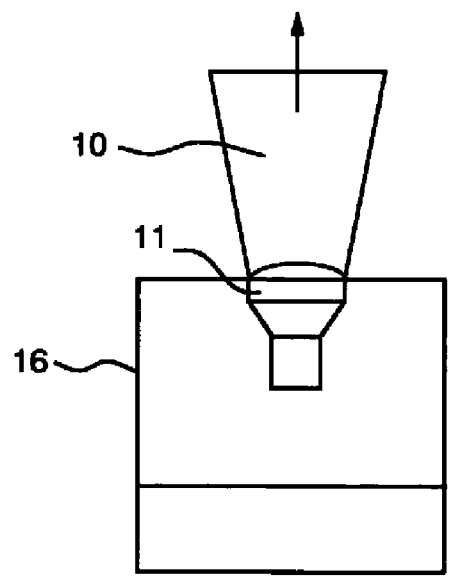

FIGS. 2 through 4 show different schematic examples of suitable isolation devices to be used in the present invention.

In FIG. 2 a funnel-shaped isolation device 10 is provided with a surface 11, e.g., a membrane, which is placed on a collection tube 12, which contains a sponge-like material 13 that serves to absorb the lysis and washing buffers. Under the sponge-like material 13 a superabsorbent layer 14 may be placed to improve the vacuum performance. Alternatively layer 14 may also contain a material which is chemically able to react with water, e.g., acrylate. The water is therefore also removed from the process. Lysate or another preparation of nucleic acids is placed in the funnel. The sponge-like material 13 absorbs the applied liquid through membrane 11. Prior to the addition of the elution buffer, the sponge is moved some distance from the membrane, e.g. by a mechanism inside collection tube 12 (not shown in the figure). This will prevent the elution buffer in the last step from being suctioned off through membrane 11. Most of the elution buffer stays on the surface (FIG. 1b) and can be removed together with the nucleic acids from above. When using this assembly the vacuum mechanism 5 in the automatic apparatus is no longer necessary.

FIG. 3 shows another example of an isolation device, which is connected to a collection tube 16 via a Luer-connection located at the bottom via a Luer-adapter 17, which in this case does not contain a sponge but is connected to a vacuum mechanism via a muff 18. Lysis and washing buffers may in this case be suctioned through membrane 11 by applying a vacuum. When the elution buffer is introduced, the vacuum remains turned off, so that the eluate can be removed from the top. With the use of a Luer-connection, individual isolation devices can be removed from the isolation device assembly. One should not forget, however, that the vacuum collection tube can also be combined with fixed isolation devices.

FIG. 4 shows an embodiment which provides for a collection tube, into which the buffers are suctioned through by way of gravity or centrifuged. The eluate buffer, which is used in small volumes, is not heavy enough in and of itself to penetrate membrane 11 and can again be removed from the top.

The procedure described above is illustrated by the following examples. In this regard, Examples 1 to 17 essentially involve the use of hydrophobic surfaces, and Examples 18 to 19 the use of hydrophilic surfaces. Different and various ways of using the procedures will be evident to the skilled practitioner from the foregoing description and from the examples. These examples and the corresponding description are presented solely for the purpose of illustration and are not to be regarded as limitations on the invention.

Example 1

Isolation of Total RNA from HeLa Cells

Commercially available hydrophobic nylon membranes (for example, a material from MSI: Magna SH with a pore diameter of 1.2 µm or a material from Pall GmbH: Hydrolon with a pore diameter of 1.2 µm) which have been made hydrophobic by means of a chemical post-treatment were placed in a plastic column in a single layer. The membranes were placed on a polypropylene grid which serves as a mechanical support. The membranes were fixed in the plastic column with a ring.

The column prepared in this manner was connected by means of a Luer connection to a vacuum chamber. All the isolation steps were conducted through the application of a vacuum.

For the isolation, $5 \times 10^5$ HeLa cells were pelletized by centrifugation. The cells were lysed by the addition of 150 µl of a commercial guanidinium isothiocyanate buffer (RLT buffer from Qiagen GmbH, Hilden Del.) according to standard procedures. The lysis was promoted by roughly mixing by pipetting or vortexing for about 5 sec. Then 150 µl of 70% ethanol were added and mixed in by pipetting or by vortexing for about 5 sec.

The lysate was then transferred into the plastic column and suctioned through the membrane by evacuating the vacuum chamber. Under the conditions thus created, the RNA remained bound to the membrane. Next, washing was carried out with a first commercial washing buffer containing guanidinium isothiocyanate (e.g., with RW1 buffer, Qiagen GmbH), and, after that, with a second washing buffer containing IRIS or TRIS and alcohol (e.g., with RPE buffer, Qiagen GmbH). The washing buffers in each case were suctioned through the membrane by evacuation of the vacuum chamber. After the final washing step, the vacuum was maintained for a period of about 10 min., in order to dry the membrane, after which the vacuum was switched off.

For the elution, 70 µl of RNase-free water was transferred onto the membrane in order to release the purified RNA from the membrane. After incubation for one minute at a temperature in the range from 10° to 30° C., the eluate was transferred from the membrane from the top and the elution step was repeated in order to make sure that the elution was complete.

Figure 5:
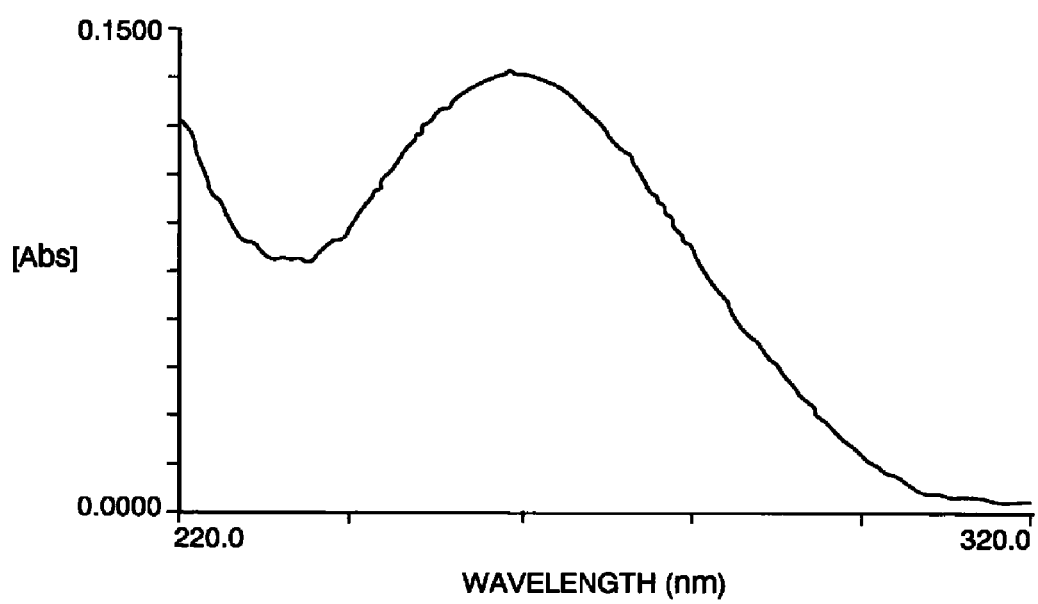
FIG. 5 plots the Absorbance of a RNA sample in the range of 220 nm to 320 nm.

The volume of isolated total RNA obtained in this manner was then determined by spectrophotometric measurement of the light absorption with a wavelength of 260 nm. The ratio between the absorbance values at 260 and 280 nm gives an estimate of RNA purity (see FIG. 5: Total RNA isolated through Hydrolon 1.2).

The results of the two isolations with hydrophobic nylon membranes (Nos. 1 and 2) are shown in Table 1, compared with experiments in which on the one hand a hydrophilic nylon (Nyaflo) (No. 3) and a silica membrane (No. 4) were used. The values reported in the table provide convincing support for the impressive isolation yield and separation effect of the materials used in accordance with the invention. They also show that silica gel-fleece produces clearly less yield, which presumably can be attributed to its fleecelike structure and the ensuing absorption of a large portion of the eluate buffer.

TABLE 1

RNA yield and purity of the total RNA isolated in accordance with Example 1

| No. | Type of membrane | Yield of Total RNA (µg) | $E_{260}/E_{280}$ |
|---|---|---|---|
| 1 | Magna SH 1.2 µm (hydrophobic nylon) | 6.0 | 1.97 |
| 2 | Hydrolon 1.2 µm (hydrophobic nylon) | 7.1 | 2.05 |
| 3 | Nyaflo (hydrophilic nylon) | <0.2 | Not determined |
| 4 | Hydrophilic silica membrane | <0.2 | Not determined |

The isolated RNA can also be analyzed on agarose gels that have been stained with ethidium bromide. For this purpose, for example, 1.2% formaldehyde agarose gels were assembled. The results are shown in FIG. 6.

Figure 6:
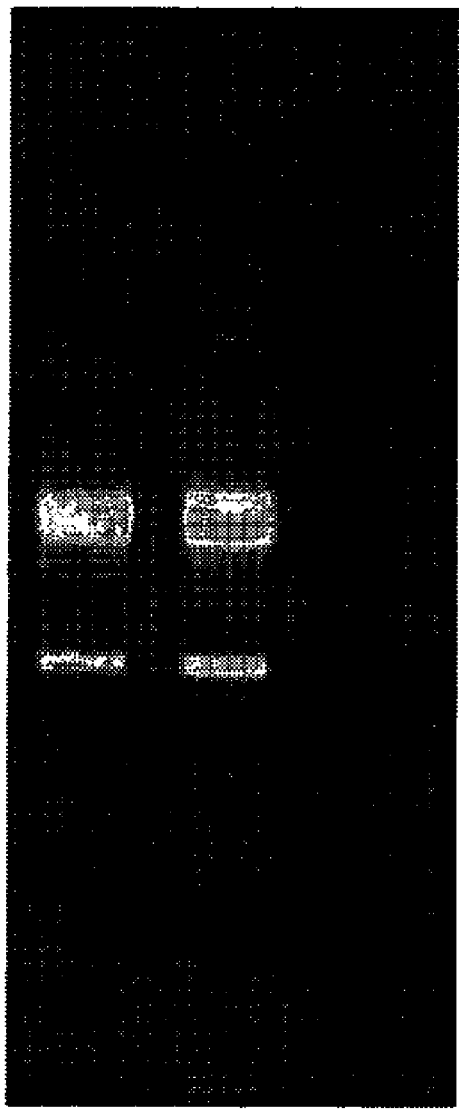
FIG. 6 shows the ethidium bromide stained gel of an electrophoretic separation of various samples according to the process of the invention.

In FIG. 6, Lane 1 is total RNA that was isolated by means of a hydrophobic nylon membrane from Magna SH with a pore diameter of 1.2 µm.

Lane 2 is total RNA that was isolated by means of a hydrophobic nylon membrane from Hydrolon with a pore diameter of 1.2 µm.

Lane 3 represents the chromatogram of total RNA that was isolated by means of a silica membrane.

In each case, 50 µl of the total RNA isolate was analyzed.

FIG. 6 provides convincing evidence that when a silica membrane is used, no measurable proportion of the total RNA can be isolated.

Example 2

Isolation of Free RNA by Binding the RNA to Hydrophobic Membranes by Means of Various Salt-Alcohol Mixtures In this example, the lysate and washing solutions were conducted through the hydrophobic membrane by applying a vacuum.

Hydrophobic nylon membranes (for example, 1.2 µm Hydrolon from the Pall Company) were introduced into plastic columns that were connected to a vacuum chamber, in a manner similar to that of Example 1.

100 µl of an aqueous solution containing total RNA was mixed, by pipetting, with 350 µl of a commercially available lysis buffer containing guanidium isothiocyanate (for example, the RLT buffer from Qiagen GmbH), 350 µl of 1.2 M sodium acetate solution, 350 µl 2 M sodium chloride solution and 350 µl of 4 M lithium chloride solution. Next, 250 µl of ethanol was added to each mixture and mixed in, likewise by pipetting. After that, the solutions containing RNA were transferred into the plastic columns and suctioned through the membrane by evacuating the vacuum chamber. Under the conditions described, the RNA remained bound to the membranes. The membranes were then washed as described in Example 1.

Finally, the RNA (also as described in Example 1) was removed from the membrane by pipetting from the top.

The volume of isolated total RNA was determined by spectrophotometric measurement of the light absorption at 260 nm. The ratio between the absorbance values at 260 and 280 nm gives an estimate of RNA purity.

TABLE 2

Isolation of free RNA by binding the RNA to hydrophobic membranes by means of various salt-alcohol mixtures

| No. | Salt-alcohol mixture | Yield of Total RNA (µg) | $E_{260}/E_{280}$ |
|---|---|---|---|
| 1 | Qiagen RLT buffer/35% ethanol | 9.5 | 1.92 |
| 2 | 0.6 M sodium acetate/35% ethanol | 8.5 | 1.98 |
| 3 | 1.0 M sodium chloride/35% ethanol | 7.9 | 1.90 |
| 4 | 2 M lithium chloride/35% ethanol | 4.0 | 2.01 |

Example 3

Isolation of Total RNA from HeLa-Cells

Commercially available hydrophobic nylon membranes were placed in a plastic column in a single layer. The membranes were placed on a polypropylene grid which served as a mechanical support. The membranes were fixed in the plastic column with a ring. The column prepared in this manner was placed in a collection tube. All the isolation steps were conducted using centrifugation.

For the isolation, $5\times10^5$ HeLa cells were pelletized by centrifugation and the supernatant substance removed. The cells were lysed by the addition of 150 µl of a commercial guanidium isothiocyanate buffer (for example RLT buffer, Qiagen GmbH) in a manner thoroughly familiar in the art. Lysis was promoted by roughly mixing by pipetting or vortexing over a period of about 5 sec. Then 150 µA of 70% ethanol were added and mixed in by pipetting or by vortexing over a period of about 5 sec.

The lysate was subsequently transferred into the plastic column and passed through the membrane by way of centrifugation at 10000×g for 1 minute. Subsequently, washing was performed with a commercially available washing buffer containing guanidinium isothiocyanate, e.g., with the RW1-buffer (Qiagen GmbH), followed by a second washing buffer containing Tris and alcohol, e.g., RPE buffer (Qiagen GmbH). The washing buffers were passed through the membrane by centrifugation. The last washing step was performed at 20000×g for 2 minutes to dry the membrane.

For the elution, 70 µl RNase-free water was transferred onto the membrane in order to release the purified RNA from the membrane. After incubation for 1-2 minutes at a temperature in the range from 10° to 30° C., the eluate was transferred from the membrane from the top and the elution step was repeated in order to make sure that the elution was complete.

The volume of isolated total RNA obtained in this manner was then determined by spectrophotometric measurement of light absorption at a wavelength of 260 nm. The ratio between the absorbance values at 260 nm and 280 nm gives an estimate of RNA purity. The results of the isolations with different hydrophobic nylon membranes are shown in Table 3. 3-5 parallel tests per membrane were carried out and the average value was calculated. Using a silica membrane, no measurable volume of total RNA was isolated, if the eluate was recovered by removing it from the top from the membrane.

TABLE 3

RNA yield of total RNA by binding to hydrophobic membranes

| Manufacturer | Membrane | Material | RNA (µg) | $E_{260}/E_{280}$ |
|---|---|---|---|---|
| Pall Gelman Sciences | Hydrolon, 1.2 µm | hydrophobic nylon | 6.53 | 1.7 |
| Pall Gelman Sciences | Hydrolon, 3 µm | hydrophobic nylon | 9.79 | 1.72 |
| Pall Gelman Sciences | Fluoro Trans G | hydrophobic carboxylated polyvinylidene difluoride | 6.16 | 1.72 |
| Pall Gelman Sciences | NFWA | acryl polymer on a nylon fabric supporting body | 2.91 | 1.73 |
| Pall Gelman Sciences | Hemasep V Medium | modified polyester | 4.16 | 1.74 |
| Pall Gelman Sciences | Hemadyne | modified polyester | 6.67 | 1.65 |
| Pall Gelman Sciences | V-800 R | slightly hydrophobic modified acryl copolymer | 6.26 | 1.72 |
| Pall Gelman Sciences | Supor-450 PR | hydrophobic polyether sulfone | 3.96 | 1.76 |
| Pall Gelman Sciences | Versapor-1200R | slightly hydrophobic modified acryl copolymer | 6.23 | 1.68 |
| Pall Gelman Sciences | Versapor-3000R | slightly hydrophobic modified acryl copolymer | 3.54 | 1.74 |
| Pall Gelman Sciences | Zefluor | polytetrafluorethylene | 5.19 | 1.65 |
| Pall Gelman Sciences | Polypro-450 | polyester fiber | 4.58 | 1.77 |
| GORE-TEX | Polypropylene Perforated Foil 9337 | hydrophobic polytetrafluorethylene | 3.6 | 1.59 |
| GORE-TEX | Polypropylene Perforated Foil 9336 | hydrophobic polytetrafluorethylene | 2.15 | 1.65 |
| GORE-TEX | Polypropylene Perforated Foil 9335 | hydrophobic polytetrafluorethylene | 1.59 | 1.72 |
| GORE-TEX | Polyester Fleece 9316 | hydrophobic polytetrafluorethylene | 3.61 | 1.69 |
| GORE-TEX | Polypropylene Fleece 9317 | hydrophobic polytetrafluorethylene | 2.87 | 1.70 |
| Millipore | Mitex Membrane | hydrophobic polytetrafluorethylene | 1.98 | 1.62 |
| Millipore | DVHP | hydrophobic polyvinylidene fluoride | 7.45 | 1.72 |
| MSI | Magna-SH, 1.2 µm | hydrophobic nylon | 4.92 | 1.69 |
| MSI | Magna-SH, 5 µm | hydrophobic nylon | 10.2 | 1.71 |
| MSI | Magna-SH, 10 µm | hydrophobic nylon | 7.36 | 1.76 |
| MSI | Magna-SH, 20 µm | hydrophobic nylon | 7.04 | 1.65 |

Example 4

Isolation of Free RNA from an Aqueous Solution

According to the procedure of Example 1, plastic columns were assembled with different hydrophobic membranes.

100 µl of an aqueous solution containing total RNA were mixed with 350 µl of a commercially available lysis buffer containing guanidinium-isothiocyanate, e.g., RLT buffers by Qiagen GmbH. Subsequently 250 µl of ethanol were added and mixed by pipetting. This mixture was then transferred to the column and passed through the membrane by way of centrifugation (10000×g for 1 minute. The membranes were subsequently washed twice with a buffer, e.g., RPE buffer by Qiagen GmbH. The buffer was passed through the membranes by way of centrifugation. The last washing step was carried out at 20000×g to dry the membranes. Subsequently, the RNA, as described in Example 3, was eluted with RNase-free water and removed from the membrane from the top by pipetting.

The volume of isolated total RNA was subsequently determined by spectrophotometric measurement of the light absorption at a wavelength of 260 nm and 280 nm. The ratio between the absorbance values at 260 nm and 280 nm gives an estimate of RNA purity.

The isolation results with various hydrophobic membranes are listed in Table 4 below. 3-5 parallel tests per membrane were carried out and the average value was calculated. Using a silica membrane, no measurable volume of total RNA was isolated, if the eluate is recovered from the membrane by removing it from the top.

TABLE 4

Isolation of free RNA from an aqueous solution by binding to hydrophobic membranes

| Manufacturer | Membrane | Material | RNA (µg) | $E_{260}/E_{280}$ |
|---|---|---|---|---|
| Pall Gelman Sciences | Hydrolon, 1.2 µm | hydrophobic nylon | 5.15 | 1.75 |
| Pall Gelman Sciences | Hydrolon, 3 µm | hydrophobic nylon | 0.22 | 1.79 |
| Pall Gelman Sciences | Fluoro Trans G | hydrophobic carboxylated polyvinylidene difluoride | 5.83 | 1.79 |
| Pall Gelman Sciences | NFWA | acryl polymer on nylon fabric supporting body | 1.85 | 1.72 |
| Pall Gelman Sciences | Hemasep V Medium | modified polyester | 4 | 1.79 |
| Pall Gelman Sciences | Hemadyne | modified polyester | 0.47 | 2.1 |
| Pall Gelman Sciences | V-800 R | slightly hydrophobic modified acryl copolymer | 2.74 | 1.77 |
| Pall Gelman Sciences | Supor-450 PR | hydrophobic polyether sulfone | 5.97 | 1.71 |
| Pall Gelman Sciences | Zefluor | polytetrafluorethylene | 8.67 | 1.69 |
| Pall Gelman Sciences | Polypro-450 | polyester fiber | 5.09 | 1.78 |
| GORE-TEX | Polypropylene Perforated Foil 9337 | hydrophobic polytetrafluorethylene | 5.96 | 1.62 |
| GORE-TEX | Polypropylene Perforated Foil 9336 | hydrophobic polytetrafluorethylene | 7.43 | 1.71 |
| GORE-TEX | Polypropylene Perforated Foil 9335 | hydrophobic polytetrafluorethylene | 4.35 | 1.63 |
| GORE-TEX | Polyester Fleece 9316 | hydrophobic polytetrafluorethylene | 5.92 | 1.67 |
| GORE-TEX | Polypropylene Fleece 9317 | hydrophobic polytetrafluorethylene | 8.7 | 1.66 |
| Millipore | Fluoropore PTFE | hydrophobic polytetrafluorethylene | 8.46 | 1.70 |
| Millipore | DVHP | hydrophobic polyvinylidene fluoride | 4.23 | 1.8 |
| MSI | Magna-SH, 1.2 µm | hydrophobic nylon | 1.82 | 1.76 |

TABLE 5

RNA yield of isolated total RNA by binding to hydrophobic membranes with different pore sizes.

| Manufacturer | Membrane | Material | Pore Size (µm) | RNA (µg) | $E_{260}/E_{280}$ |
|---|---|---|---|---|---|
| Infiltec | Polycon 0.01 | Hydrophilic Polycarbonate | 0.01 | 0.17 | 1.64 |
| Pall | Fluoro Trans G | Hydrophobic Polyvinylidene difluoride | 0.2 | 6.16 | 1.72 |
| Pall | Supor-450 PR | Hydrophobic Polyethersulfone | 0.45 | 3.96 | 1.76 |
| Millipore | Durapore | Hydrophobic Polyvinylidene fluoride | 0.65 | 7.45 | 1.72 |
| MSI | Magna-SH | Hydrophobic Nylon | 1.2 | 4.92 | 1.69 |
| MSI | Magna-SH | Hydrophobic Nylon | 5 | 10.2 | 1.71 |
| MSI | Magna-SH | Hydrophobic Nylon | 10 | 7.36 | 1.76 |
| MSI | Magna-SH | Hydrophobic Nylon | 20 | 7.04 | 1.65 |

Example 5

Isolation of Total RNA from HeLa Cells Depending on the Membrane's Pore Size

According to the procedures of Example 1 plastic columns were assembled with different hydrophobic membranes with different pore sizes.

According to Example 3, a cell lysate was made from $5 \times 10^5$ HeLa-cells and transferred to the columns. Subsequently the membranes were washed with commercially available buffers (RW1 and RPE from Qiagen GmbH). The last centrifugation step was carried out at 20000×g for 2 minutes to dry the membrane. The elution was carried out as described in Example 1. The results are listed in Table 5 below. 3-5 parallel tests per membrane were performed and the average value calculated for each.

Example 6

Isolation of Genomic DNA from an Aqueous Solution

According to Example 3, plastic columns were assembled with hydrophobic membranes (e.g. Magna-SH, 5 µm by the MSI Company). Purification was carried out with commercial buffers from Qiagen GmbH.

200 µl of an aqueous solution of genomic DNA from liver tissue were introduced in PBS buffers. 200 µl of a buffer containing guanidinium hydrochloride, e.g., Qiagen's AL buffer, were added to and mixed with this solution. Subsequently 210 µl of ethanol were added and mixed by vortexing. The mixture was transferred to the column according to Example 3 and passed through the membrane by way of centrifugation. The membrane was then washed and dried with an alcohol-containing buffer, e.g., Qiagen's RW buffer. The elution was performed as described in Example 3. Three parallel tests were carried out and the average value calculated. The amount of isolated DNA was subsequently determined by spectrophotometric measurement of the light absorption at a wavelength of 260 nm and was approx. 30% of the starting amount. The absorption ratio at 260 nm to 280 nm was 1.82.

Example 7

Isolation of Genomic DNA from Tissue

According to Example 3, plastic columns were assembled with hydrophobic membranes (e.g. Magna-SH, 5 µm by MSI). Purification was carried out with commercially available buffers from Qiagen GmbH (Hilden, Del.).

180 µl of ATL-buffer were added to 10 mg of kidney tissue (mouse) and ground in a mechanical homogenizer. Subsequently proteinase K (approx. 0.4 mg eluted in 20 µl of water) were added and left to incubate for 10 minutes at 55° C. After adding 200 µl of a buffer containing guanidinium hydrochloride (AL buffer by Qiagen), and after a 10 minute incubation at 70° C., 200 µl of ethanol were added and mixed with this solution. This mixture was placed on the column and passed through the membrane by centrifugation. The membrane was then washed with alcohol containing buffers, e.g., AW1 and RW by Qiagen, and subsequently dried by way of centrifugation. The elution was carried out as described in Example 3.

Three parallel tests were carried out and the average value calculated. The amount of isolated DNA was subsequently determined by spectrophotometric measurement of the light absorption at a wavelength of 260 nm and is on average 9.77 μg. The absorption ratio at 260 nm to 280 nm was 1.74.

Example 8

Immobilization of Total RNA from an Aqueous Solution Using Different Chaotropic Agents According to Example 3, plastic columns were assembled with hydrophobic membranes.

100 μl of an aqueous solution containing total RNA were mixed with 350 μl of different lysis buffers, which contained guanidinium isothiocyanate (GITC) or guanidinium hydrochloride (GuHCl) in different concentrations. Subsequently 250 μl ethanol were added and mixed by pipetting. This mixture was then placed on the column and passed through the membrane by centrifugation (10000×g; 1 minute). The membranes were subsequently washed twice with an alcohol-containing buffer, e.g., RPE by Qiagen. The buffer was passed through the membrane by centrifugation. The last washing step was performed at 20000×g to dry the membranes. The elution was carried out as described in Example 3. Two tests were carried out to determine the average value. The results are listed in Table 6.

TABLE 6

RNA yield from an aqueous solution using different chaotropic agents

| Membrane | Chaotropic Agents and Concentration in Binding Solution | Yield of Total RNA (μg) |
|---|---|---|
| Hydrolon, 1.2 μm | GITC, 500 mM | 2.3 |
| Hydrolon, 1.2 μm | GITC, 1 M | 0.8 |
| Hydrolon, 1.2 μm | GITC, 3 M | 0.9 |
| Fluoro Trans G | GITC, 500 mM | 0.4 |
| Fluoro Trans G | GITC, 1 M | 1.25 |
| Fluoro Trans G | GITC, 3 M | 0.6 |
| Hydrolon, 1.2 μm | GuHCl, 500 mM | 2.6 |
| Hydrolon, 1.2 μm | GuHCl, 1 M | 6.7 |
| Hydrolon, 1.2 μm | GuHCl, 3 M | 2.9 |
| Fluoro Trans G | GuHCl, 500 mM | 0.4 |
| Fluoro Trans G | GuHCl, 1 M | 1.25 |
| Fluoro Trans G | GuHCl, 3 M | 0.6 |

Example 9

Immobilization of Total RNA from an Aqueous Solution with the Use of Different Alcohols According to Example 3, plastic columns were assembled with hydrophobic membranes. 100 μl of an aqueous solution containing total RNA were mixed with 350 μl of a lysis buffer containing guanidinium isothiocyanate (concentration 4 M). Subsequently, different amounts of ethanol and isopropanol were added and loaded with RNase-free water up to 700 μl and mixed. This mixture was then transferred to the column and passed through the membrane and washed according to Example 3. The elution took place as in Example 3.

Two tests are carried out and the average value determined. The results are listed in Table 7.

TABLE 7

RNA-yield from an aqueous solution with different alcohols in a binding solution

| Membrane | Alcohol and Concentration in Binding Solution | Yield of Total RNA (μg) |
|---|---|---|
| Hydrolon, 1.2 μm | Ethanol, 5% | 0.7 |
| Hydrolon, 1.2 μm | Ethanol, 30% | 2.85 |
| Hydrolon, 1.2 μm | Ethanol, 50% | 4.5 |
| DVHP | Ethanol, 5% | 0.4 |
| DVHP | Ethanol, 30% | 1.25 |
| DVHP | Ethanol, 50% | 0.6 |
| Hydrolon, 1.2 μm | Isopropanol, 5% | 0.35 |
| Hydrolon, 1.2 μm | Isopropanol, 30% | 4.35 |
| Hydrolon, 1.2 μm | Isopropanol, 50% | 3.2 |
| DHVP | Isopropanol, 10% | 1.35 |
| DHVP | Isopropanol, 30% | 4.1 |
| DHVP | Isopropanol, 50% | 3.5 |

Example 10

Immobilization of Total RNA from an Aqueous Solution with Various pH-Values

According to Example 3, plastic columns are assembled with hydrophobic membranes. 100 μl of an aqueous solution containing total RNA are mixed with 350 μl of a lysis buffer containing guanidinium isothiocyanate (concentration 4 M). The buffer contains 25 mM of sodium citrate and is adjusted to different pH-values by way of HCl or NaOH. Subsequently 250 μl of ethanol are added and mixed. This mixture is then transferred to the column and passed through the membrane and washed according to Example 4. The elution also took place as in Example 3. Two tests are carried out to determine the average value.

The results are listed in Table 8.

TABLE 8

RNA-yield from an aqueous solution with various pH-values in a binding solution

| Membrane | pH-Value in Binding Solution | Yield of Total RNA (μg) |
|---|---|---|
| Hydrolon, 1.2 μm | pH 3 | 0.15 |
| Hydrolon, 1.2 μm | pH 9 | 1.6 |
| Hydrolon, 1.2 μm | pH 11 | 0.05 |
| Fluoro Trans G | pH 1 | 0.45 |
| Fluoro Trans G | pH 9 | 2.85 |
| Fluoro Trans G | pH 11 | 0.25 |

Example 11

Immobilization of Total RNA from an Aqueous Solution with Various Salts

According to Example 3, plastic columns are assembled with hydrophobic membranes. 100 μl of a total RNA containing aqueous solution are mixed with 350 μl of a salt containing lysis buffer (NaCl, KCL, MgSO$_4$). Subsequently 250 μl of H$_2$O or ethanol are added and mixed. This mixture is then transferred to the column and passed through the membrane, washed and eluted according to Example 4. Two tests are carried out to determine the average value.

The results are listed in Table 9.

TABLE 9

RNA-yield from an aqueous solution with various salts in a binding solution

| Membrane | Salt Concentration in Binding Solution | Yield of Total RNA (µg) |
|---|---|---|
| Hydrolon, 1.2 µm | NaCl, 100 mM; without ethanol | 0.1 |
| Hydrolon, 1.2 µm | NaCl, 1 M; without ethanol | 0.15 |
| Hydrolon, 1.2 µm | NaCl, 5 M; without ethanol | 0.3 |
| Hydrolon, 1.2 µm | KCl, 10 mM; without ethanol | 0.2 |
| Hydrolon, 1.2 µm | KCl, 1 M; without ethanol | 0.1 |
| Hydrolon, 1.2 µm | KCl, 3 M; without ethanol | 0.25 |
| Hydrolon, 1.2 µm | MgSO$_4$, 100 mM; without ethanol | 0.05 |
| Hydrolon, 1.2 µm | MgSO$_4$, 750 mM; without ethanol | 0.15 |
| Hydrolon, 1.2 µm | MgSO$_4$, 2 M; without ethanol | 0.48 |
| Hydrolon, 1.2 µm | NaCl, 500 mM; with ethanol | 2.1 |
| Hydrolon, 1.2 µm | NaCl, 1 M; with ethanol | 1.55 |
| Hydrolon, 1.2 µm | NaCl, 2.5 M; with ethanol | 1.35 |
| Hydrolon, 1.2 µm | KCl, 500 mM; with ethanol | 1.6 |
| Hydrolon, 1.2 µm | KCl, 1 M; with ethanol | 2.1 |
| Hydrolon, 1.2 µm | KCl, 1.5 M; with ethanol | 3.5 |
| Hydrolon, 1.2 µm | MgSO$_4$, 10 mM; with ethanol | 1.9 |
| Hydrolon, 1.2 µm | MgSO$_4$, 100 mM; with ethanol | 4.6 |
| Hydrolon, 1.2 µm | MgSO$_4$, 500 M; with ethanol (sic!) | 2 |

Example 12

Immobilization of Total RNA from an Aqueous Solution by Way of Various Buffer Conditions According to Example 3, plastic columns were assembled with hydrophobic membranes.

100 µl of an aqueous solution containing total RNA were mixed with 350 µl of a lysis buffer containing guanidinium isothiocyanate (concentration 2.5 M). The lysis buffer was mixed with various concentrations of sodium citrate, pH 7, or sodium oxalate, pH 7.2. Subsequently 250 µl of ethanol are added and mixed. This mixture was then transferred to the column and passed through the membrane according to Example 4 and washed and eluted.

The results are listed in Table 10. Two tests were carried out to determine the average value.

TABLE 10

RNA yield from an aqueous solution with various buffer concentrations in a binding solution

| Membrane | Na-Citrate in the Lysis Buffer | Yield of Total RNA (µg) |
|---|---|---|
| Hydrolon, 1.2 µm | Na-Citrate, 10 mM | 2.2 |
| Hydrolon, 1.2 µm | Na-Citrate, 100 mM | 2.4 |
| Hydrolon, 1.2 µm | Na-Citrate, 500 mM | 3.55 |
| Supor-450 PR | Na-Citrate, 10 mM | 1.1 |
| Supor-450 PR | Na-Citrate, 100 mM | 1.15 |
| Supor-450 PR | Na-Citrate, 500 mM | 0.2 |
| Hydrolon, 1.2 µm | Na-Oxalate, 1 mM | 1.5 |
| Hydrolon, 1.2 µm | Na-Oxalate, 25 mM | 1.05 |
| Hydrolon, 1.2 µm | Na-Oxalate, 50 mM | 0.9 |
| Supor-450 PR | Na-Oxalate, 1 mM | 1.9 |
| Supor-450 PR | Na-Oxalate, 25 mM | 1.3 |
| Supor-450 PR | Na-Oxalate, 50 mM | 1.7 |

Example 13

Immobilization of Total RNA from an Aqueous Solution by Means of Phenol

As in Example 3, plastic columns with hydrophobic membranes (e.g., Hydrolon, 1.2 µm from the company Pall Gelman Sciences) were constructed.

An aqueous RNA solution was mixed with 700 µl of phenol and distributed across the membranes by means of centrifugation. As in Example 4, the membranes were washed and the RNA eluted. Double measurements were carried out, and in each case the average value indicated. The ratio between the absorbance values at 260 and 280 nm gives an estimate of RNA purity. The amount of isolated RNA is subsequently determined by photometric measurement of the light absorption at a wavelength of 260 nm and is on average 10.95 µg. The absorption ratio at 260 nm to the one at 280 nm is 0.975.

Example 14

Washing of Immobilized Total RNA Under Different Salt Concentrations

According to Example 3, plastic columns were assembled with hydrophobic membranes.

100 µl of an aqueous solution containing total RNA are mixed with 350 µl of a lysis buffer containing guanidinium isothiocyanate (concentration 4 M). Subsequently, 250 µl of ethanol were added and mixed. This mixture was then transferred to the column and passed through the membrane according to Example 4. The membranes were then washed twice with a buffer which contains various concentrations of NaCl and 80% ethanol. The buffer was passed through the membrane by centrifugation. The last washing step was carried out at 20000×g in order to dry the membranes. The elution also takes place according to Example 3. Two tests were carried out to determine the average value.

The results are listed in Table 11.

TABLE 11

RNA-yield from an aqueous solution with NaCl in the washing buffer

| Membrane | NaCl in the Washing Buffer | Yield of Total RNA (µg) |
|---|---|---|
| Hydrolon, 1.2 µm | NaCl, 10 mM | 1.4 |
| Hydrolon, 1.2 µm | NaCl, 50 mM | 3.15 |
| Hydrolon, 1.2 µm | NaCl, 100 mM | 3 |
| DHVP | NaCl, 10 mM | 2.7 |
| DHVP | NaCl, 50 mM | 2.85 |
| DHVP | NaCl, 100 mM | 2.7 |

Example 15

Elution of Immobilized Total RNA Under Different Salt and Buffer Conditions

According to Example 3, plastic columns were assembled with hydrophobic membranes.

100 µl of an aqueous solution containing total RNA were mixed with 350 µl of a lysis buffer containing guanidinium isothiocyanate (concentration 4 M). Subsequently 250 µl of ethanol were added and mixed. This mixture was then transferred to the column and passed through the membrane and washed according to Example 3.

For elution, 70 µl of a NaCl containing solution, a Tris/HCl-buffer (pH 7) or a sodium oxalate solution (pH 7.2) were pipetted onto the membrane, in order to elute the purified RNA from the membrane. After 1 to 2 minutes of incubation, at a temperature between 10°-30° C., the eluate was pipetted from the top from the membrane. The elution step was repeated once in order to achieve complete elution. Two tests were carried out to determine the average value.

The results are summarized in Table 12.

TABLE 12

RNA-yield from an aqueous solution with NaCl or Tris/HCl in the elution buffer

| Membrane | NaCl or Tris in the Elution Buffer | Yield of Total RNA (µg) |
| --- | --- | --- |
| Hydrolon, 1.2 µm | NaCl, 1 mM | 1.35 |
| Hydrolon, 1.2 µm | NaCl, 50 mM | 1.2 |
| Hydrolon, 1.2 µm | NaCl, 250 mM | 0.45 |
| DVHP | NaCl, 1 mM | 0.9 |
| DVHP | NaCl, 50 mM | 0.35 |
| DVHP | NaCl, 500 mM | 0.15 |
| Hydrolon, 1.2 µm | Tris 1 mM | 0.35 |
| Hydrolon, 1.2 µm | Tris 10 mM | 0.75 |
| DVHP | Tris 1 mM | 1.5 |
| DVHP | Tris 50 mM | 1 |
| DVHP | Tris 250 mM | 0.1 |
| Hydrolon, 1.2 µm | Na-Oxalate, 1 mM | 0.45 |
| Hydrolon, 1.2 µm | Na-Oxalate, 10 mM | 0.65 |
| Hydrolon, 1.2 µm | Na-Oxalate, 50 mM | 0.3 |
| DVHP | Na-Oxalate, 1 mM | 2 |
| DVHP | Na-Oxalate, 10 mM | 0.155 |
| DVHP | Na-Oxalate, 50 mM | 0.15 |

Example 16

Use of Total RNA in a 'Real Time' Quantitative RT-PCR with the Use of 5' Nuclease PCR-Assay to Amplify and Detect β-Actin mRNA According to Example 3, plastic columns were assembled with a commercially available membrane (Pall Gelman Sciences, Hydrolon with a pore size of 1.2 µm).

To isolate RNA, $1 \times 10^5$ HeLa cells were used and the purification of total RNA was carried out as described in Example 3. The elution was performed with $2 \times 60$ µl of $H_2O$ as described in Example 3. For the complete removal of remaining amounts of DNA, the sample was treated with a DNase prior to analysis.

A "one-device 'Real Time' quantitative RT-PCR" was carried out with the use of the commercially available reaction system of Perkin-Elmer (TaqMan™ PCR Reagent Kit) by using a M-MLV reverse transcriptase. Using a specific primer and a specific TaqMan™ probe for 13-Actin (TaqMan™ β-Actin Detection Kits made by Perkin Elmer) the β-Actin mRNA-molecules in the total RNA-sample were first converted into β-Actin cDNA and subsequently the total reaction was amplified and detected immediately, without interruption, in the same reaction device. The reaction specimens were produced according to the manufacturer's instructions. Three different amounts of isolated total RNA were used (1, 2, 4 µl of eluate) and triple determination tests were carried out. As a control, three samples without RNA were also tested.

The cDNA synthesis was performed at 37° C. for one hour, immediately followed by a PCR which comprised 40 cycles. The reactions and the analyses were carried out on an ABI PRISM™ 7700 Sequence Detector manufactured by Perkin Elmer Applied Biosystems. Every amplicon generated during a PCR cycle produced a light-emitting molecule, which was generated by splitting from the TaqMan™ probe. The total light signal that was generated was directly proportional to the amplicon volume that was being generated and hence proportional to the original amount of transcript available in the total RNA sample. The emitted light was measured by the apparatus and evaluated by a computer program. The PCR cycle, during which the light signal must first be detected over the background noise, was designated as the "Threshold Cycle" (ct). This value was a measure of the amount of specifically amplified RNA available in the sample.

For the 1 µl volume used of total RNA, isolated with the process described here, the result was an average ct-value of 17.1; for 2 µl in total RNA the ct-value was 16.4 and for 4 µl of total RNA the ct-value was 15.3. This resulted in a linear dependency between the total RNA and the ct-value, which indicates that the total RNA was free of substances that might inhibit the amplification reaction. The control specimens containing no RNA did not produce any signals.

Example 17

Use of Total RNA in an RT-PCR for Amplification and Detection of β-Actin mRNA

According to Example 3, plastic columns were assembled with commercially available membranes (Pall Gelman Sciences, Hydrolon with a pore size of 1.2 or 3 µm; Sartorius, SARTOLON® polyamide filter membrane with a pore size of 0.45 µm).

For isolation of RNA, two different starting materials were used:
1) total RNA from liver (mouse) in an aqueous solution; the purification of total RNA and the elution were carried out as described in Example 4; and
2) $5 \times 10^5$ HeLa cells, the purification of total RNA and the elution were carried out as described in Example 3.

For each test, 20 ng of isolated total RNA were used. As a control, RNA purified using RNEASY® RNA isolation-Kits (Qiagen GmbH) and a sample without RNA were used.

A RT-PCR was performed with these samples under standard conditions. For amplification two different primer pairs were used for the β-Actin. A 150 Bp-sized fragment served as proof of sensitivity, a 1.7 kBp-sized fragment assessed the integrity of the RNA. From the RT-reaction, 1 µl was removed and transferred to the subsequent PCR. 25 cycles were performed for the small fragment and 27 cycles for the large fragment. The annealing temperature was 55° C. The amplified samples were subsequently placed on a non-denaturing gel and analyzed.

For the 20 ng volume used of total RNA isolated in the process described above, the corresponding DNA-fragments can be demonstrated in the RT-PCR. When using total RNA from mouse liver, no transcript can be demonstrated, as the conditions used here were adjusted to human β-Actin. The control specimens which contain no RNA did not produce any signals. FIG. 7 shows ethidium bromide stained gels of an electrophoretic separation of RT-reactions.

Figure 7A:
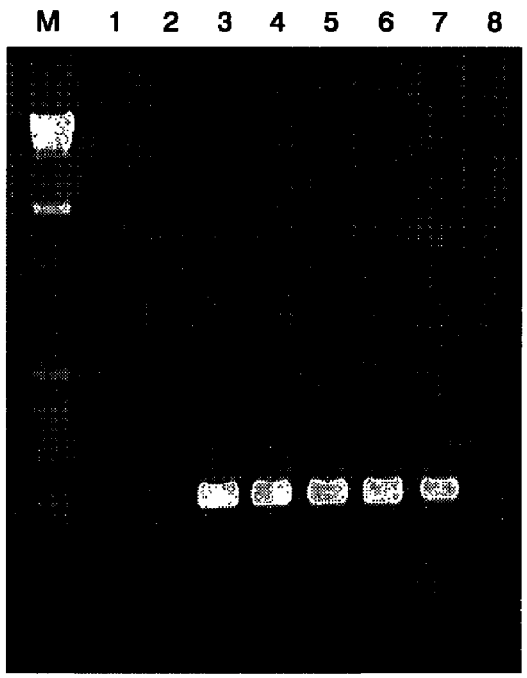
FIG. 7 shows another ethidium bromide stained gel of an electrophoretic separation of various samples according to the process of the invention.
Figure 7B:
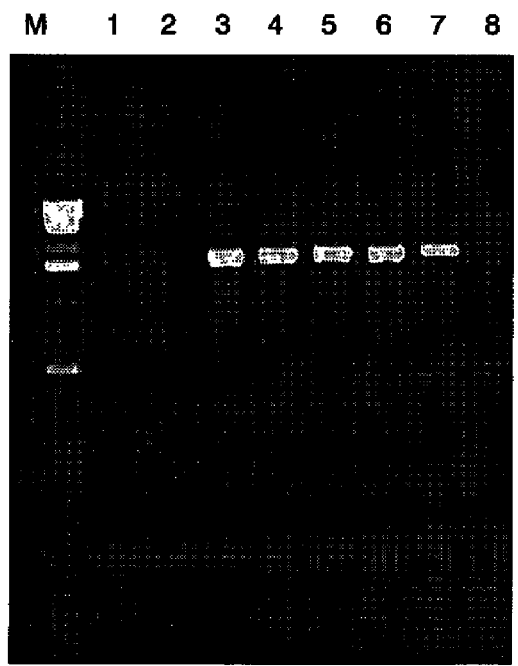

FIG. 7A: Lane 1 to 8: RT-PCR of a 150 Bp-fragment;
Lane 1, 2: RNA from an aqueous solution purified with the Hydrolon 1.2 µm membrane;
Lane 3, 4: RNA from HeLa cells purified with the SARTOLON® polyamide filter membrane;
Lane 5, 6: RNA from HeLa cells purified with the Hydrolon 3 µm membrane;

Lane 7: RNA purified by way of RNEASY® RNA isolation-Mini-Kit;
Lane 8: Control without RNA.
FIG. 7B: Lane 1 to 8: RT-PCR of a 1.7 kBp-fragment;
Lane 1, 2: RNA from an aqueous solution purified with the Hydrolon 1.2 µm membrane;
Lane 3, 4: RNA from HeLa cells purified with the SARTOLON® polyamide filter membrane;
Lane 5, 6: RNA from HeLa cells purified with the Hydrolon 3 µm membrane;
Lane 7: RNA purified by way of RNEASY® RNA isolation-Mini-Kit;
Lane 8: Control without RNA.

Example 18

Isolation of Total RNA from HeLa Cells by Binding to Hydrophilic Membranes

Commercially available hydrophilic membranes, which consist of various materials, were placed in a plastic column in a single layer. As in example 3, the membranes were placed on a polypropylene grid and fixed with a ring.

For the isolation, $5 \times 10^5$ HeLa cells were used. The isolation and the elution of the nucleic acid was carried out as described in Example 3.

The volume of isolated total RNA was subsequently determined by the spectrophotometric measurement of light absorption at a wave length of 260 nm. The ratio between the absorbance values at 260 and 280 nm gives an estimate of RNA purity.

The results of the isolations with the various hydrophilic membranes are presented in Table 13 below. 2-5 parallel experiments per membrane were carried out, and in each case an average value was calculated. Using a silica membrane, no measurable amount of total RNA was isolated if the eluate was taken from the membrane by drawing it off from the top.

TABLE 13

RNA yield of RNA isolated by binding to hydrophilic membranes on the basis of example 18

| Manufacturer | Membrane | Material | RNA (µg) | 260 nm/ 280 nm |
|---|---|---|---|---|
| Pall Gelman Sciences | I.C.E.-450 | hydrophilic polyether sulfone | 6.36 | 1.8 |
| Pall Gelman Sciences | I.C.E.-450sup | hydrophilic polyether sulfone on a polyester fabric | 3.07 | 1.71 |
| Pall Gelman Sciences | Premium Release | hydrophilic polyester membrane | 1.66 | 1.63 |
| Pall Gelman Sciences | Supor-800 | hydrophilic polyether sulfone | 4.12 | 1.7 |
| Pall Gelman Sciences | Supor-450 | hydrophilic polyether sulfone | 4.69 | 1.69 |
| Pall Gelman Sciences | Supor-100 | hydrophilic polyether sulfone | 3.25 | 1.71 |
| GORE-TEX | Polypropylene 9339 | hydrophilic polytetrafluoroethylene on a polypropylene fabric | 1.08 | 1.65 |
| GORE-TEX | Polypropylene Fleece 9338 | hydrophilic polytetrafluoroethylene on polypropylene fleece | 3.97 | 1.67 |
| GORE-TEX | Polyester Fleece 9318 | hydrophilic polytetrafluoroethylene on polypropylene fleece | 3.61 | 1.69 |

TABLE 13-continued

RNA yield of RNA isolated by binding to hydrophilic membranes on the basis of example 18

| Manufacturer | Membrane | Material | RNA (µg) | 260 nm/ 280 nm |
|---|---|---|---|---|
| Millipore | Durapore PVDF | Hydrophilisized polyvinylidene fluoride | 5.6 | 1.69 |
| Millipore | hydrophylized PTFE | hydrophilisized polytetrafluoroethylene | 3.14 | 1.66 |
| Millipore | Durapore PVDF | hydrophilisized polyvinylidene fluoride | 3.12 | 1.68 |
| Sartorius | Membrane filter Type 250 | hydrophilic polyamide | 4.3 | 1.66 |
| Infiltec | Polycon 0.01 | hydrophilic polycarbonate | 0.17 | 1.64 |
| Infiltec | Polycon 0.1 | hydrophilic polycarbonate | 0.73 | 1.68 |
| Infiltec | Polycon 1 | hydrophilic polycarbonate | 3.33 | 1.86 |

Example 19

Isolation of Free RNA from an Aqueous Solution by Binding to Hydrophilic Membranes As in Example 18, plastic columns with various hydrophilic membranes were constructed.

100 µl of an aqueous solution containing total RNA was mixed with 350 µl of a commercially available lysis buffer containing guanidinium isothiocyanate, e.g., RLT buffer (Qiagen GmbH). Then, 250 µl of ethanol were added and mixed by pipetting. This mixture was then transferred to the column and passed through the membrane, washed, and dried as in Example 4.

The RNA was then eluted with RNase-free water, as described in Example 3, and drawn off from the membrane by means of a pipette.

The volume of isolated total RNA was subsequently determined by spectrophotometric measurement of light absorption at a wavelength of 260 nm, and the ratio between the absorbance values at 260 and 280 nm was determined, tgive an estimate of RNA purity. The results of the isolations with the various hydrophilic membranes are presented in Table 2b following. 2-5 parallel experiments per membrane were carried out, and in each case the average value was calculated. By using a silica membrane, no measurable amount of total RNA can be isolated if the eluate is taken from the membrane by drawing it off from the top.

TABLE 14

Isolation of free RNA from an aqueous solution by binding to hydrophilic membranes

| Manufacturer | Membrane | Material | RNA (µg) | $E_{260}/E_{280}$ |
|---|---|---|---|---|
| Pall Gelman Sciences | I.C.E.-450 | hydrophilic polyethersulfone | 1.92 | 1.82 |
| Pall Gelman Sciences | I.C.E.-450sup | hydrophilic polyether sulfone on polyester webbing | 0.87 | 1.67 |
| Pall Gelman Sciences | Supor-800 | hydrophilic polyether sulfone | 3.93 | 1.74 |
| Pall Gelman Sciences | Supor-450 | hydrophilic polyether sulfone | 1.78 | 1.74 |

TABLE 14-continued

Isolation of free RNA from an aqueous solution by binding to hydrophilic membranes

| Manufacturer | Membrane | Material | RNA (µg) | $E_{260}/E_{280}$ |
|---|---|---|---|---|
| Pall Gelman Sciences | Supor-100 | hydrophilic polyether sulfone | 1.04 | 1.68 |
| GORE-TEX | Polypro-pylene 9339 | hydrophilic polytetrafluorethylene on a polypropylene fabric | 0.43 | 1.48 |
| GORE-TEX | Polypro-pylene Fleece 9338 | hydrophilic polytetrafluorethylene on a polypropylene fleece | 3.63 | 1.64 |
| GORE-TEX | Polyester Fleece 9318 | hydrophilic polytetrafluorethylene on polypropylene fleece | 5.92 | 1.67 |
| Millipore | Durapore PVDF | hydrophilisized polyvinylidene fluoride | 1.18 | 1.79 |
| Millipore | PTFE made hydrophilic | hydrophilisized polytetrafluorethylene | 2.84 | 1.72 |
| Sartorius | Membrane filter Type 250 | hydrophilic polyamide | 2.7 | 1.7 |

The invention claimed is:

1. A process for isolating nucleic acids comprising the following steps:
charging a non-siliceous membrane from a given direction with nucleic acids, wherein said nonsiliceous membrane has two opposing sides;
immobilizing the nucleic acids on one side of the non-siliceous membrane by binding the nucleic acids to said one side of the membrane in the presence of an immobilization buffer;
releasing the immobilized nucleic acids from the non-siliceous membrane by applying an elution agent wherein the released nucleic acids do not pass through to the other side of the non-siliceous membrane; and
removing the released nucleic acids from the same side of the non-siliceous membrane on which the nucleic acids were immobilized,
wherein the released nucleic acids are removed without retrieving materials that have contacted the other side of said non-siliceous membrane, and wherein the membrane has pores that have a diameter of 1 µm to 50 µm.

2. The process according to claim 1, wherein, between the immobilization and release steps, a washing of the immobilized nucleic acids with at least one washing buffer takes place without releasing the nucleic acids from the membrane.

3. The process according to claim 2, wherein the washing includes the following steps for each washing buffer:
transferring a predetermined amount of washing buffer to the non-siliceous membrane, and
drawing the washing buffer through the non-siliceous membrane by suction or centrifugation.

4. The process according to claim 1 further comprising the following steps:
mixing of the nucleic acids with the immobilization buffer;
charging of the nucleic acids mixed with the immobilization buffer on to the non-siliceous membrane;
drawing the fluid components of the mixture through the non-siliceous membrane.

5. The process according to claim 1 or claim 3, wherein at least one of the steps is carried out completely automatically by means of an automatic machine.

6. The process according to claim 5, wherein all the steps in the process are carried out by an automatic machine in a controlled sequence.

7. The process according to claim 5, wherein multiple isolations of nucleic acids are carried out simultaneously using a multiplicity of membranes.

8. The process according to claim 1, characterized by the fact that between the release and the removal steps at least one chemical reaction is carried out on the nucleic acids.

9. The process according to claim 4, wherein said immobilization buffer includes aqueous solutions of salts of alkaline and alkaline earth metals with mineral acids.

10. The process according to claim 9, wherein said immobilization buffer includes alkaline or alkaline earth halogenides or sulfate.

11. The process according to claim 10, wherein said immobilization buffer includes halogenides of sodium or potassium or magnesium sulfate.

12. The process according to claim 4, wherein the immobilization buffer includes aqueous solutions of salts of monobasic or polybasic or polyfunctional organic acids with alkaline or alkaline earth metals.

13. The process according to claim 12, wherein said aqueous solutions of salts of polyfunctional organic acids with alkaline or alkaline earth metals includes aqueous solutions of salts of sodium, potassium, or magnesium with organic dicarboxylic acids.

14. The process according to claim 13, wherein said organic dicarboxylic acid is oxalic acid, malonic acid, or succinic acid.

15. The process according to claim 12, wherein said aqueous solutions of salts of polyfunctional organic acids with alkaline or alkaline earth metals includes aqueous solutions of salts of sodium or potassium in combination with hydroxycarboxylic or polyhydroxycarboxylic acid.

16. The process according to claim 15, wherein said polyhydroxycarboxylic acid is citric acid.

17. The process according to claim 4, wherein said immobilization buffer includes a phenol or polyphenol.

18. The process according to claim 1, wherein the releasing step is carried out using an aqueous salt or buffer solution.

19. The process according to claim 1, wherein the nucleic acids immobilized on the non-siliceous membrane are released using water.

20. The process according to claim 4, wherein said immobilization buffer comprises an aqueous solution of a chaotropic agent.

21. The process according to claim 20, wherein the chaotropic agent is selected from the group consisting of trichloroacetates, thiocyanates, perchlorates, iodides, guanidinium hydrochloride, guanidinium isothiocyanate, and urea.

22. The process according to claim 20, wherein said immobilization buffer comprises a 0.01-molar to 10-molar aqueous solution of the chaotropic agent.

23. The process according to claim 22, wherein said immobilization buffer comprises a 0.1-molar to 7-molar aqueous solution of the chaotropic agent.

24. The process according to claim 23, wherein said immobilization buffer comprises a 0.2-molar to 5-molar aqueous solution of the chaotropic agent.

25. The process according to any one of claims 20 through 24, wherein said immobilization buffer comprises an aqueous solution of sodium perchlorate, guanidinium hydrochloride, guanidinium isothiocyanate, sodium iodide, or potassium iodide.

26. The process according to claim 1, wherein the membrane is a hydrophobic membrane.

27. The process according to claim 26, wherein the hydrophobic membrane is made of a polymer with polar groups.

28. The process according to claim 1, wherein the membrane is a hydrophilic membrane with a hydrophobized surface.

29. The process according to claim 1, wherein the membrane is composed of a polymeric material selected from the group consisting of nylon, a polysulfone, polyether sulfone, polycarbonate, polyacrylate, acrylic acid copolymer, polyurethane, polyamide, polyvinyl chloride, polyfluorocarbonate, polytetrafluoroethylene, polyvinylidene fluoride, polyvinylidene difluoride, polyethylene tetrafluoroethylene copolymerisate, polyethylene chlorotrifluoroethylene copolymerisate, and polyphenylene sulfide.

30. The process according to claim 29, wherein the nylon is hydrophobized nylon.

31. The process according to claim 29, wherein the membrane is coated with a hydrophobic coating agent selected from the group consisting of paraffins, waxes, metallic soaps, quaternary organic compounds, urea derivates, lipid-modified melamine resins, organic zinc compounds, and glutaric dialdehyde.

32. The process according to claim 1, wherein the membrane is a hydrophilic or hydrophilized membrane.

33. The process according to claim 32, wherein the membrane is composed of hydrophilized nylon, polyether sulfone, polycarbonate, polyacrylate, acrylic acid copolymer, polyurethane, polyamide, polyvinyl chloride, polyfluorocarbonate, polytetrafluoroethylene, polyvinylidene fluoride, polyvinylidene difluoride, polyethylene tetrafluoroethylene copolymerisate, polyethylene chlorotrifluoroethylene copolymerisate, or polyphenylene sulfide.

34. A process for isolating nucleic acids comprising:
(1) immobilizing nucleic acids on one side of a non-siliceous membrane by binding the nucleic acids to said one side of the membrane in the presence of an immobilization buffer, followed by
(2) releasing the immobilized nucleic acids from the membrane by applying to the membrane an elution agent, wherein the eluted nucleic acids do not pass through to the other side of the non-siliceous membrane; and
(3) collecting the released nucleic acids from the same side of the membrane on which the nucleic acids were immobilized;
wherein the nucleic acids are collected without retrieving materials that have contacted said other side of said membrane; wherein the membrane comprises a material selected from the group consisting of nylon, polysulfone, polyether sulfone, polycarbonate, polyacrylate, acrylic acid copolymer, polyurethane, polyamide, polyvinyl chloride, polyfluorocarbonate, polytetrafluoroethylene, polyvinylidene fluoride, polyvinylidene difluoride, polyethylene tetrafluoroethylene copolymerisate, polyethylene chlorodifluoroethylene copolymerisate, and polyphenylene sulfide; wherein the membrane material is hydrophilic, hydrophobic, hydrophilisized, or hydrophobisized; and wherein the membrane has pores that have a diameter of 1 μm to 50 μm.

35. The process according to claim 34, wherein the membrane is a hydrophobisized nylon membrane.

36. The process according to claim 34, wherein the membrane is a hydrophilic membrane, which is coated with a hydrophobic coating agent selected from the group consisting of paraffins, waxes, metallic soaps, quaternary organic compounds, urea derivates, lipid-modified melamine resins, organic zinc compounds, and glutaric dialdehyde.

37. The process according to claim 34, wherein said process for isolating nucleic acids is carried out in a plurality of isolation devices installed on a multi-well plate.

38. The process according to claim 2, wherein the washing step is carried out using an aqueous solution of a salt of an alkaline or alkaline earth metal with a mineral acid.

39. The process according to claim 2, wherein the washing step is carried out using an aqueous solution of a salt from a monobasic, polybasic, or polyfunctional organic acid with an alkaline or alkaline earth metal.

40. The process according to claim 2, wherein the washing step is carried out using an aqueous solution of a chaotropic agent.

41. The process according to claim 2, wherein the washing step is carried out using a hydroxyl derivative of an aliphatic or acyclic saturated or unsaturated hydrocarbon.

42. The process according to claim 2, wherein the washing step is carried out using a phenol or a polyphenol.

43. The process according to claim 31 or claim 36, wherein said metallic soaps are in admixture with aluminum or zirconium salts.

44. The process according to claim 34, further comprising the steps of:
mixing the nucleic acids with said immobilization buffer,
charging the nucleic acids mixed with said immobilization buffer onto the membrane,
optionally, washing the nucleic acids immobilized on the membrane,
drawing the unbound fluid components of the mixture or wash buffer through the membrane.

45. The process according to claim 44, wherein said immobilization buffer includes aqueous solutions of salts of alkaline and alkaline earth metals with mineral acids.

46. The process according to claim 44, wherein said immobilization buffer includes aqueous solutions of salts of monobasic or polybasic or polyfunctional organic acids with alkaline or alkaline earth metals.

47. The process according to claim 44, wherein said immobilization buffer includes hydroxyl derivatives of aliphatic or acyclic saturated or unsaturated hydrocarbons.

48. The process according to claim 44, wherein said immobilization buffer includes a phenol or polyphenol.

49. The process according to claim 34 or claim 44, wherein a chaotropic agent is used for the immobilization of the nucleic acids.

50. The process according to claim 34 or claim 44, wherein said C1-C5 alkanol is selected from the group consisting of methanol, ethanol, n-propanol, isopropanol, tert.-butanol, and pentanols.

51. The process according to claim 1, wherein the non-siliceous membrane is oriented so that one of the two opposing sides of the non-siliceous membrane is on top of the other side so that the nucleic acids are charged on and removed from the top side of the non-siliceous membrane.

52. The process according to claim 4, wherein the immobilization buffer includes hydroxyl derivates of aliphatic or acyclic saturated or unsaturated hydrocarbons.

53. The process according to claim 52, wherein said hydroxyl derivatives are $C_1$-$C_5$ alkanols.

54. The process according to claim 53, wherein said $C_1$-$C_5$ alkanol is selected from the group consisting of methanol, ethanol, n-propanol, isopropanol, tert.-butanol, and pentanols.

55. The process according to claim 52, wherein said hydroxyl derivative is an aldite.

56. The process according to claim 1, wherein a chaotropic agent is used for the immobilization buffer.

57. The process according claim 56, wherein the chaotropic agent is selected from the group consisting of trichloroacetates, thiocyanates, perchlorates, iodides, guanidinium hydrochloride, guanidinium isothiocyanate, and urea.

58. The process according to claim 56, wherein a 0.01 molar to 10 molar aqueous solution of the chaotropic agent is used for the immobilization buffer.

59. The process according to claim 58, wherein a 0.1 molar to 7 molar aqueous solution of the chaotropic agent is used for the immobilization buffer.

60. The process according to claim 59, wherein a 0.2 molar to 5 molar aqueous solution of the chaotropic agent is used for the immobilization buffer.

61. The process according to anyone of claims 56-60, wherein the chaotropic agent is selected from the group consisting of sodium perchlorate, guanidinium hydrochloride, guanidinium isothiocyanate, sodium iodide, and potassium iodide.

62. The process according to any one of claims 4, 34, 35-37, and 44, wherein the immobilization buffer has a pH of from 3 to 11.

63. The process according to claim 1, wherein the membrane has pores that range from 1 to 20 micrometers in diameter.

64. The process according to claim 1, wherein the membrane has pores that range from 1 to 10 micrometers in diameter.

65. The process according to claim 1, wherein the membrane has pores that have a diameter of at least 1 µm.

66. The process according to claim 1, wherein the membrane has pores that have a diameter of at least 1.2 µm.

67. The process according to claim 1, wherein the membrane has pores that have a diameter of at least 3 µm.

68. The process according to claim 1, wherein the membrane has pores that have a diameter of at least 5 µm.

69. The process according to claim 1, wherein the membrane has pores that have a diameter of at least 10 µm.

70. The process according to claim 1, wherein the membrane has pores that have a diameter of at least 20 µm.

* * * * *